(12) United States Patent
Chen et al.

(10) Patent No.: US 8,859,301 B2
(45) Date of Patent: Oct. 14, 2014

(54) SYSTEM AND METHOD FOR STEP COVERAGE MEASUREMENT

(71) Applicant: Intermolecular, Inc., San Jose, CA (US)

(72) Inventors: Hanhong Chen, Milpitas, CA (US);
Edward Haywood, San Jose, CA (US);
Pragati Kumar, Santa Clara, CA (US)

(73) Assignee: Intermolecular, Inc., San Jose, CA (US)

( * ) Notice: Subject to any disclaimer, the term of this patent is extended or adjusted under 35 U.S.C. 154(b) by 0 days.

(21) Appl. No.: 13/914,848

(22) Filed: Jun. 11, 2013

(65) Prior Publication Data

US 2013/0272496 A1      Oct. 17, 2013

Related U.S. Application Data

(63) Continuation of application No. 12/946,846, filed on Nov. 15, 2010, now Pat. No. 8,486,727.

(51) Int. Cl.
  *G01R 31/26*    (2014.01)
  *H01L 21/66*    (2006.01)
  *G01N 23/223*    (2006.01)

(52) U.S. Cl.
  CPC .............. *G01N 23/223* (2013.01); *H01L 22/12* (2013.01)

USPC .......................................................... 438/14

(58) Field of Classification Search
  None
  See application file for complete search history.

(56) References Cited

U.S. PATENT DOCUMENTS

| | | | |
|---|---|---|---|
| 6,351,516 B1 * | 2/2002 | Mazor et al. | 378/44 |
| 6,879,051 B1 * | 4/2005 | Singh et al. | 257/798 |
| 7,718,447 B2 * | 5/2010 | Zienert et al. | 438/16 |
| 8,486,727 B2 * | 7/2013 | Chen et al. | 438/14 |

* cited by examiner

*Primary Examiner* — Seahvosh Nikmanesh

(57) ABSTRACT

Determining an unknown step coverage of a thin film deposited on a 3D wafer includes exposing a planar wafer comprising a first film deposited thereon to X-ray radiation to create first fluorescent radiation; detecting the first fluorescent radiation; measuring a number of XRF counts on the planar wafer; creating an XRF model of the planar wafer; providing a portion of the 3D wafer comprising troughs and a second film deposited thereon; determining a multiplier factor between the portion of the 3D wafer and the planar wafer; exposing the portion of the 3D wafer to X-ray radiation to create second fluorescent radiation; detecting the second fluorescent radiation; measuring a number of XRF counts on the portion of the 3D wafer; calculating a step coverage of the portion of the 3D wafer; and determining a uniformity of the 3D wafer based on the step coverage of the portion of the 3D wafer.

8 Claims, 12 Drawing Sheets

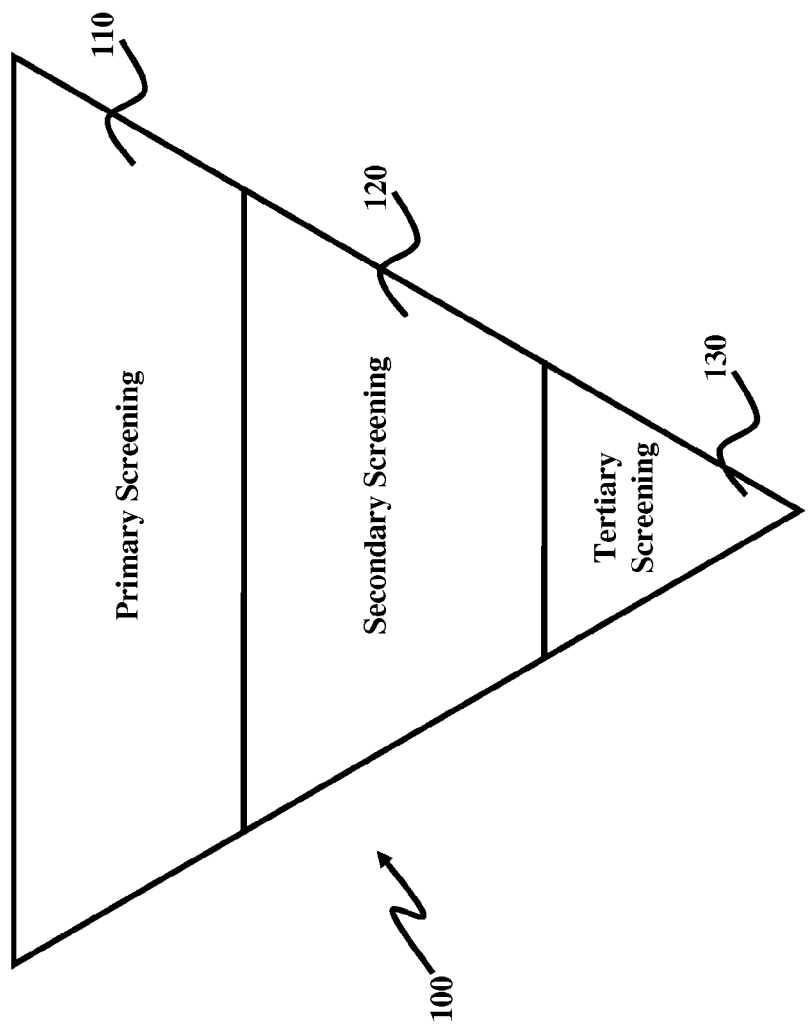

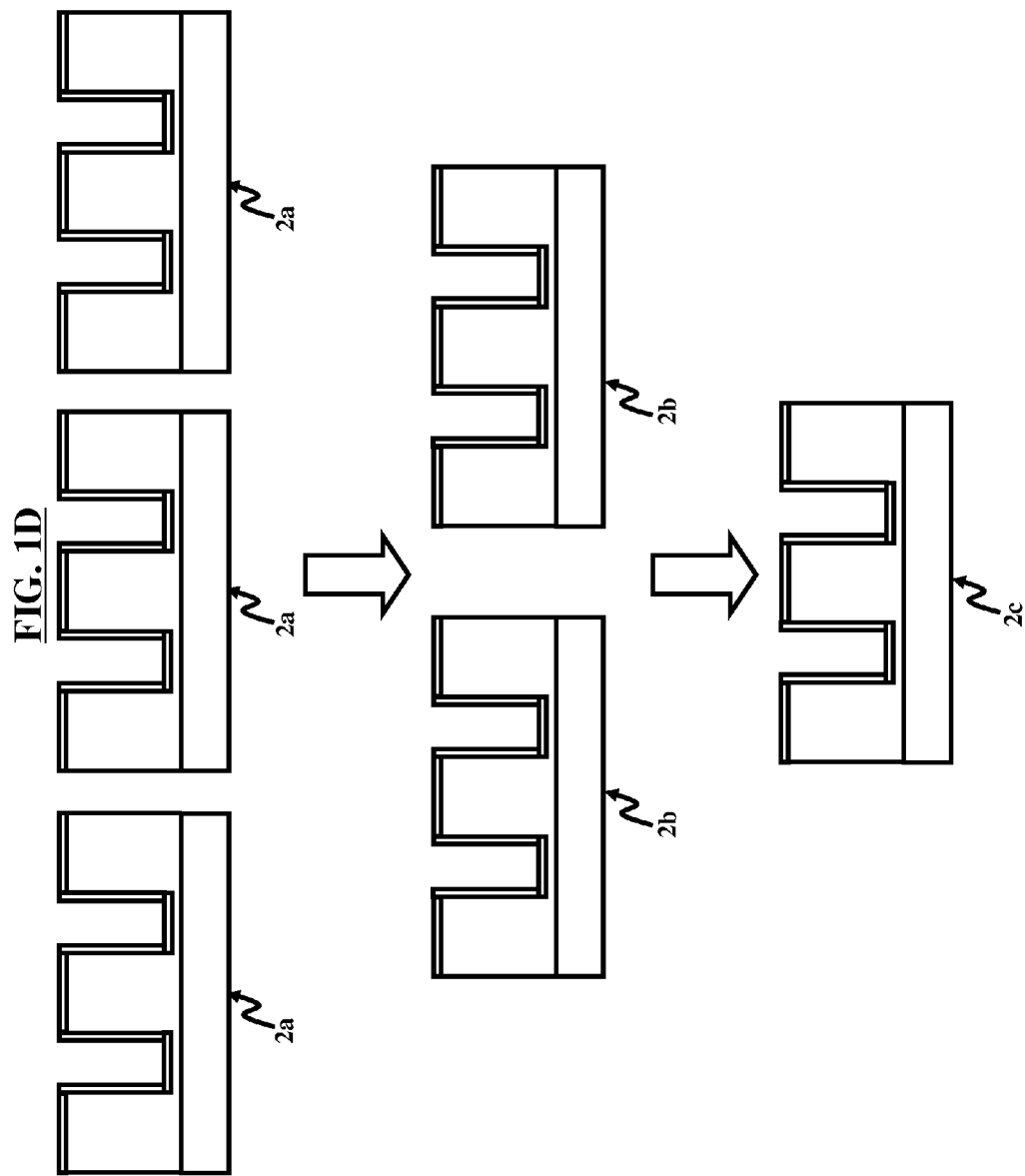

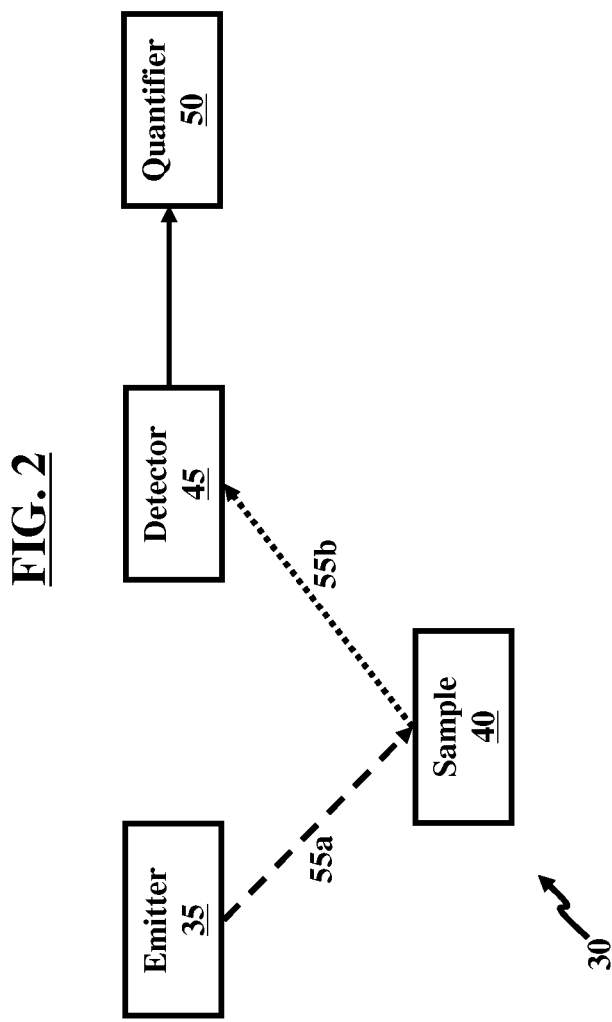

SYSTEM AND METHOD FOR STEP COVERAGE MEASUREMENT

CROSS-REFERENCE TO RELATED APPLICATIONS

This application is a continuation claiming priority to U.S. patent application Ser. No. 12/946,846, now U.S. Pat. No. 8,486,727, filed Nov. 15, 2010 and incorporated herein by reference for all purposes.

BACKGROUND

1. Technical Field

The embodiments herein generally relate to semiconductor processing technologies, and more specifically, to high throughput metrology methods used to determine the coverage of a thin film over patterned features in semiconductor processing technologies.

2. Description of the Related Art

The ability to process uniformly across a monolithic substrate and/or across a series of monolithic substrates is advantageous for manufacturing efficiency and cost effectiveness, as well as repeatability and control. However, uniform processing across an entire substrate can be disadvantageous when optimizing, qualifying, or investigating new materials, new processes, and/or new process sequence integration schemes, since the entire substrate is nominally made the same using the same materials, processes, and process sequence integration schemes. Each processed substrate generally represents, in essence, only one possible variation per substrate. Thus, the full wafer uniform processing under conventional processing techniques results in fewer data points per substrate, longer times to accumulate a wide variety of data, and higher costs associated with obtaining such data.

Conventional techniques generally do not efficiently screen and analyze an array of materials, processes, and process sequence integration schemes across a substrate, and thus typically do not efficiently evaluate alternative materials, processes, and process sequence integration schemes for semiconductor manufacturing processes.

BRIEF DESCRIPTION OF THE DRAWINGS

The embodiments herein will be better understood from the following detailed description with reference to the drawings, in which:

FIG. 1A illustrates a schematic diagram of a combinatorial screening process according to an embodiment herein;

FIG. 1D illustrates a schematic diagram of the combinatorial screening process shown in FIG. 1A applied to the second step coverage measurement shown in FIG. 1C, according to an embodiment herein;

FIG. 2 illustrates a block diagram of a step coverage measurement tool according to an embodiment herein;

DETAILED DESCRIPTION

Figure 1B:
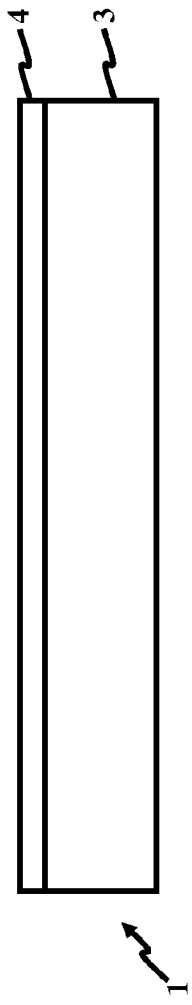
FIG. 1B illustrates a schematic diagram of a first step coverage measurement according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Referring now to the drawings, and more particularly to FIGS. 1A through 9, there are shown embodiments herein. The manufacturing of integrated circuits (IC) semiconductor devices, flat panel displays, optoelectronics devices, data storage devices, magneto electronic devices, magneto optic devices, packaged devices, solar devices, and the like entails the integration and sequencing of many unit processing steps. For example, IC manufacturing typically includes a series of processing steps such as cleaning, surface preparation, deposition, lithography, patterning, etching, planarization, implantation, thermal annealing, and other related unit processing steps. The precise sequencing and integration of the unit processing steps enable the formation of functional devices meeting desired performance specifications such as speed, power consumption, yield, and reliability. Furthermore, the tools and equipment employed in device manufacturing have been developed to enable the processing of ever-increasing substrate sizes such as the move to twelve inch (or 300 millimeter) diameter wafers in order to fit more ICs per substrate per unit processing step for productivity and cost benefits. Other methods of increasing productivity and decreasing manufacturing costs include the use of batch reactors whereby multiple monolithic substrates can be processed in parallel. In these processing steps, a monolithic substrate or a batch of monolithic substrates are processed uniformly; i.e., in the same fashion with the same resulting physical, chemical, electrical, and the like properties across a given monolithic substrate.

The embodiments herein support and enable efficient combinatorial processing. For example, in an embodiment described below, combinatorial processing provides rapid evaluation of semiconductor processing operations. Some exemplary semiconductor processing operations include operations for adding (depositions) and removing layers (etching), defining features, preparing layers (e.g., cleans), doping, etc. In such an embodiment, the systems supporting the combinatorial processing are flexible to accommodate the demands for running the different processes either in parallel, serial, or some combination of the two.

As used herein, combinatorial processing may include any processing (e.g., semiconductor processing) that varies the processing conditions in two or more regions of a substrate. A substrate may be, for example, a silicon substrate such as a wafer that is used in semiconductor processing. A region of a substrate may be any portion of the substrate that is somehow defined, for example by dividing the substrate into regions having predetermined dimensions or by using physical barriers, such as sleeves, over the substrate. The region may or may not be isolated from other regions. For example, a substrate may be divided into two or more regions, each of which may or may not include semiconductor device structures (e.g., metallization such as interconnects and vias, active elements such as transistors, etc.). A process may be performed at each of the regions. For example, a first region is cleaned using a first cleaning agent, and a second region is cleaned using a second cleaning agent. The efficacies of the two cleaning agents are evaluated, and none, one, or both of the cleaning agents may be selected as suitable candidates for larger scale processing (e.g., on regions with structures or regions enabling more sophisticated testing or a full wafer). According to other examples, multiple iterations of the same experiment are performed on the same substrate, and any number of regions may be defined. For example, five cleaning solutions may be tested using fifteen regions of a substrate, each cleaning solution being tested three times.

As described above, combinatorial processing, when applied to semiconductor manufacturing operations, enables multiple experiments to be performed on a single substrate. Equipment for performing the combinatorial processing and characterization of the combinatorial test substrates must support the efficiency offered through the combinatorial processing operations. Consequently, a valuable, quick, and efficient combinatorial processing component is the characterization tool(s) used to produce the data from the high throughput experimentation in such a way that the process does not slow down.

The process of forming semiconductor test substrates to combinatorially test materials, processes, and devices is described herein. Combinatorial processing enables multiple experiments to be performed on a single substrate and the rapid evaluation of processing operations and materials. The semiconductor test substrates are designed to run the different combinatorial processes either in parallel, serial, or some combination of the two. These methodologies all incorporate the formation of site-isolated regions using a combinatorial processing tool and the use of these site-isolated regions to form the test area (e.g., metal/insulator/metal systems (MIMS), such as memory devices). Therefore, multiple MIMS may be rapidly formed on a single substrate for use in combinatorial methodologies. Any of the individual processes of the methods described herein may be varied combinatorially to test varied process conditions or materials.

Use of combinatorial-based rapid device prototyping methods permits fabrication, comprehensive characterization, and analysis of hundreds of unique MIMS on a weekly basis to dramatically increase productivity and learning rates. For example, knowledge about alternative device structures, process integration schemes, and material compositions can be systematically explored at speeds that would otherwise be impossible using traditional methods and tools.

As described above, during one embodiment of combinatorial processing, each wafer is subjected to many different process conditions. FIG. 1A illustrates an example of such a combinatorial screening process 100. As shown in FIG. 1A, combinatorial screening process 100 includes primary screening process (110), secondary screening process (120), and tertiary screening process (130). For example, numerous material compositions (e.g., 18 spots or 46 spots on a single wafer, where each spot is a unique material composition) are systematically explored on a single wafer at speeds during the primary screening process (110) that would otherwise be impossible using traditional methods and tools. Once the best materials, process conditions, or process integration for a particular high-k dielectric/MIM stack are identified using combinatorial screening methods (e.g., during primary screening process (110)), that material is then scaled up to test the step coverage of that material and/or conditions during a secondary screening process (120). Furthermore, according to one embodiment herein, additional testing may take place during a tertiary screening process (130). Due to the speed and non-destructiveness of the step coverage test (described in further detail below) occurring in secondary screening process (120), materials and/or conditions that pass both the primary screening process (110) and secondary screening process (120) can rapidly proceed to the tertiary screening process (130). Consequently, to test the step coverage of these material compositions, the embodiments herein utilize an improved measurement tool to enable the collection of information more rapidly.

Figure 1C:
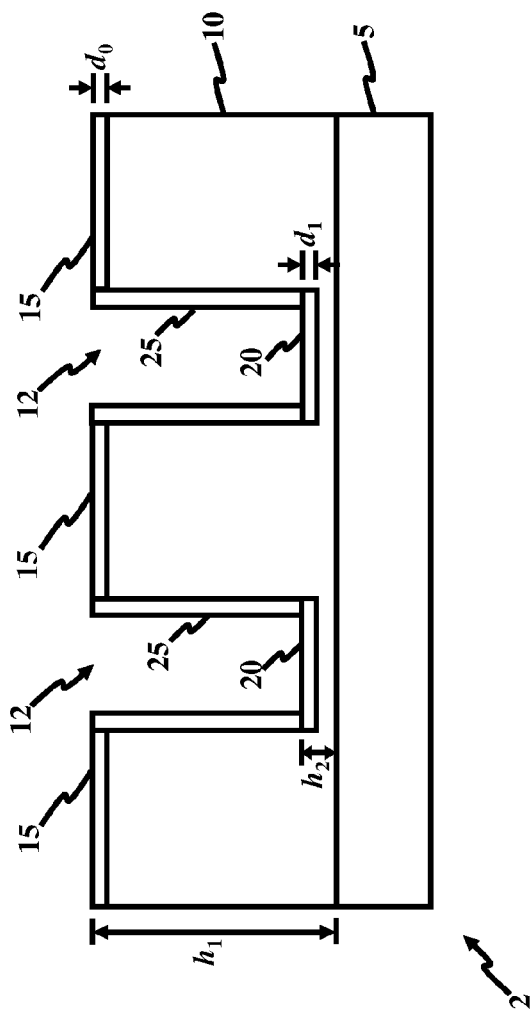
FIG. 1C illustrates a schematic diagram of a second step coverage measurement according to an embodiment herein.

FIGS. 1B and 1C, with reference to FIG. 1A, illustrate schematic diagrams of two devices (e.g., device 1 and device 2) prepared for step coverage measurement according to an embodiment herein. FIG. 1B illustrates device 1, which is a planar device that includes a planar thin film 4 deposited on a planar substrate 3. As shown in FIG. 1C, device 2 is a three-dimensional (3D) device and includes substrate 5 deposited with a material composition 10 (e.g., identified in accordance with the combinatorial processing techniques discussed above) and etched with a series of troughs 12. Covering material composition 10 are a high plateau thin film 15, a low plateau thin film 20, and a sidewall thin film 25 (e.g., zirconium oxide or $ZrO_2$ if developing memory applications). Other possible applications may need to use high aspect ratio step coverage characterization, such as barrier layer or seed layer deposition over dual damascene trenches in semiconductor logic applications, for example. According to the embodiments herein, material composition 10, high plateau thin film 15, low plateau thin film 20, and sidewall thin film 25 can be deposited using atomic layer deposition (ALD), physical vapor deposition (PVD), and chemical vapor deposition (CVD), for example. The high plateau film 15 is configured at a first height ($h_1$) from the substrate 5 and the low plateau film 20 is configured at a second height ($h_2$) from the substrate 5, wherein the second height ($h_2$) is lower than the first height ($h_1$). The sidewall thin film 25 has a thickness varying from top to bottom, with the thickness at the top of sidewall thin film 25 close in thickness to the high plateau film 15, and the thickness at the bottom of sidewall thin film 25 close in thickness to the low plateau film 20. Furthermore, according to an embodiment herein, step coverage (SC) is defined as a ratio of $$\frac{d_1}{d_0} \times 100,$$

where $d_0$ is defined as the thickness of high plateau thin film 15 and $d_1$ is defined as the thickness of low plateau thin film 20. Step coverage is an important parameter to characterize the uniformity of deposited films, particularly for substrates (e.g., wafers) that have trenches or holes with high aspect ratios (e.g., 2:1 to 18:1). For example, high step coverage is particularly desired for 3D dynamic random access memory (DRAM) capacitors.

FIG. 1D, with reference to FIGS. 1A through and 1C, illustrates a schematic diagram of the combinatorial screening process shown in FIG. 1A applied to the second step coverage measurement shown in FIG. 1C, according to an embodiment herein. As shown in FIG. 1D, devices 2a are initially screening (e.g., during a primary screening process (110)) in order to reduce the number of devices 2a that show promising characteristics. Devices 2b are those devices drawn from devices 2a that pass the initial screening (e.g., primary screening process (110)). Devices 2b are further screened (e.g., secondary screening process (120)) by subjecting devices 2b to additional testing (e.g. a step coverage test, as described below). As shown in FIG. 1D, device 2c is a subset of devices 2b that pass the additional screening (e.g., secondary screening process (120)) applied to devices 2b. Device 2c may be further screened (e.g., tertiary screening process (130)) by scaling device 2c to cover an entire wafer or coupon. According to one embodiment herein, devices 2a, 2b, and 2c each have a thin film (e.g., high plateau thin film 15, low plateau thin film 20, and sidewall thin film 25) comparable to what is illustrated in FIG. 1C.

Figure 1E:
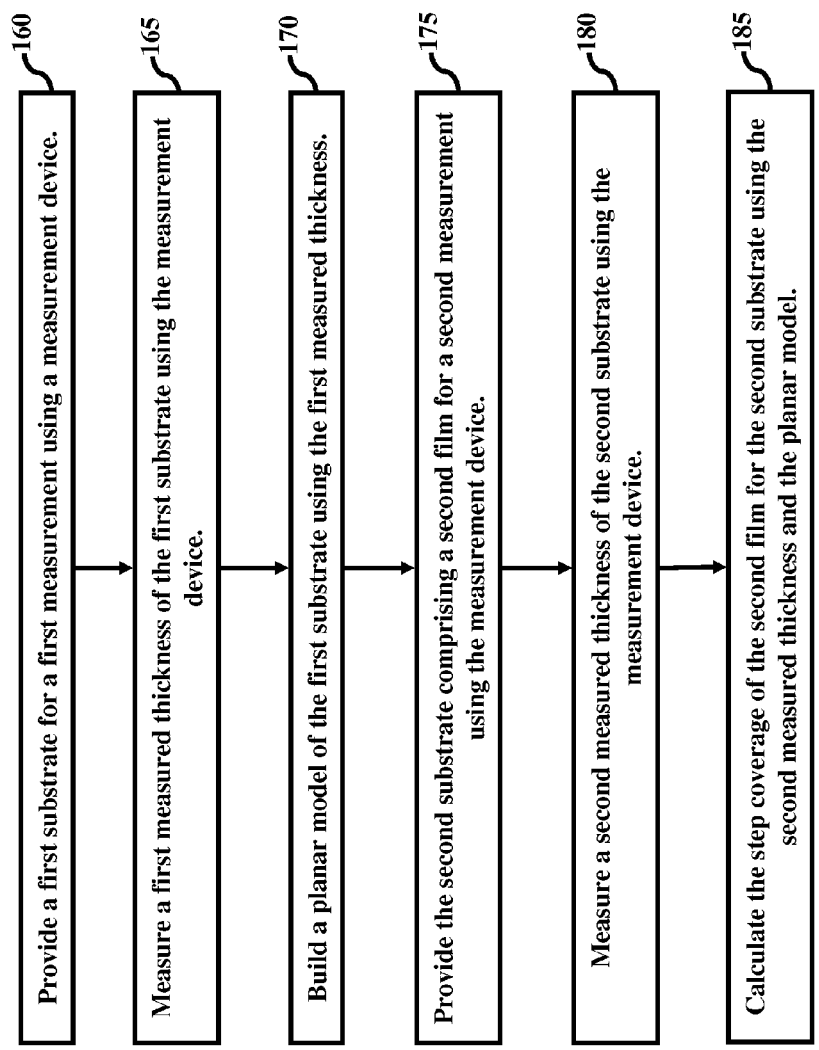
FIG. 1E illustrates a flow diagram of a testing method according to an embodiment herein.

FIG. 1E, with reference to FIGS. 1A through 1D and FIG. 2, illustrates a flow diagram of a testing method according to an embodiment herein. According to one embodiment herein, a method is shown in FIG. 1E for determining step coverage of a film (e.g., high plateau thin film 15 or low plateau thin film 20) covering a substrate (e.g., substrate 5) that includes providing (160) a first substrate (e.g., planar substrate 3) or a first measurement using a measurement device (e.g., step coverage measurement tool 30, shown in FIG. 2), wherein the first substrate (e.g., planar substrate 3) comprises a first film (e.g., planar thin film 4) deposited thereon. The next step involves measuring (165) a first measured thickness of the first substrate (e.g., planar substrate 3) using the measurement device (e.g., step coverage measurement tool 30, shown in FIG. 2), wherein the measuring by the measurement device (e.g., step coverage measurement tool 30, shown in FIG. 2) is materially non-destructive of the first substrate (e.g., planar substrate 3). Thereafter, the method includes building (170) a planar model of the first substrate (e.g., planar substrate 3) using the first measured thickness; and providing (175) the second substrate (e.g., substrate 5) comprising a second film (e.g., high plateau thin film 15 or low plateau thin film 20) covering the second substrate (e.g., substrate 5) for a second measurement using the measurement device (e.g., step coverage measurement tool 30, shown in FIG. 2), wherein the second substrate (e.g., substrate 5) comprises a first plateau (e.g., high plateau thin film 15) and a second plateau (e.g., low plateau thin film 20), wherein the first plateau (e.g., high plateau thin film 15) occupies a higher elevation on the second substrate (e.g., substrate 5) than the second plateau (e.g., low plateau thin film 20), and wherein the second film (e.g., high plateau thin film 15 or low plateau thin film 20) is deposited on the second substrate (e.g., substrate 5) and covers the first plateau (e.g., high plateau thin film 15) and the second plateau (e.g., low plateau thin film 20). Next, the method involves measuring (180) a second measured thickness of the second substrate (e.g., substrate 5) using the measurement device (e.g., step coverage measurement tool 30, shown in FIG. 2), wherein the measuring by the measurement device (e.g., step coverage measurement tool 30, shown in FIG. 2) is materially non-destructive of the second substrate (e.g., substrate 5) and the second film (e.g., high plateau thin film 15 or low plateau thin film 20). Finally, the method provides calculating (185) the step coverage of the second film (e.g., high plateau thin film 15 or low plateau thin film 20) for the second substrate (e.g., substrate 5) using the second measured thickness and the planar model.

FIG. 2, with reference to FIGS. 1A through 1E, illustrates a schematic diagram of a step coverage measurement tool 30 according to an embodiment herein. As shown in FIG. 2, step coverage measurement tool 30 includes an emitter 35, a detector 45, and a quantifier 50. In addition, during measurement, step coverage measurement tool 30 optionally includes sample 40 (e.g., high plateau thin film 15, low plateau thin film 20, and sidewall thin film 25 shown in FIG. 1C). In contrast with conventional systems (e.g., cross-sectional transmission electron microscopy (XTEM)), step coverage measurement tool 30, is a non-destructive test and thereby allows further analysis of a sample 40 following the measurement of a material's step coverage. In one embodiment herein, the step coverage measurement tool 30 includes an X-ray fluorescence (XRF) measurement device (e.g., in one embodiment, the XRF measurement device comprises emitter 35 and detector 45 shown in FIG. 2) that detects and quantifies the emission of characteristic "secondary" (or fluorescent) X-rays from sample 40 that have been excited by bombarding the sample 40 with emitted radiation 55a (e.g., high-energy X-rays or gamma rays) from emitter 35. When the materials of sample 40 (e.g., high plateau thin film 15, low plateau thin film 20, and sidewall thin film 25 shown in FIG. 1C) are exposed to emitted radiation 55a (e.g., short-wavelength X-rays or to gamma rays), the ionization of component atoms in the films 15, 20, 25 takes place. Ionization includes the ejection of one or more electrons from an atom, and takes place when the atom is exposed to radiation with an energy amount greater than its ionization potential (e.g., emitted radiation 55a). According to an embodiment herein, emitted radiation 55a expels tightly held electrons from the inner orbitals of atoms in sample 40 (e.g., high plateau thin film 15, low plateau thin film 20, and sidewall thin film 25 shown in FIG. 1C). The removal of an electron in this way renders the electronic structure of such an atom unstable, and electrons in higher orbitals migrate to a lower orbital to fill holes left behind. During this migration, energy is released in the form of a photon; the energy of which is equal to the energy difference of the two orbitals involved. Consequently, in step coverage measurement tool 30, the sample 40 emits fluorescent radiation 55b, which has the energy characteristic of the atoms present. Fluorescent radiation 55b is subsequently detected by detector 45 and then quantified by quantifier 50 (e.g., a proportional counter measurement device, a photomultiplier, etc.).

Figure 3:
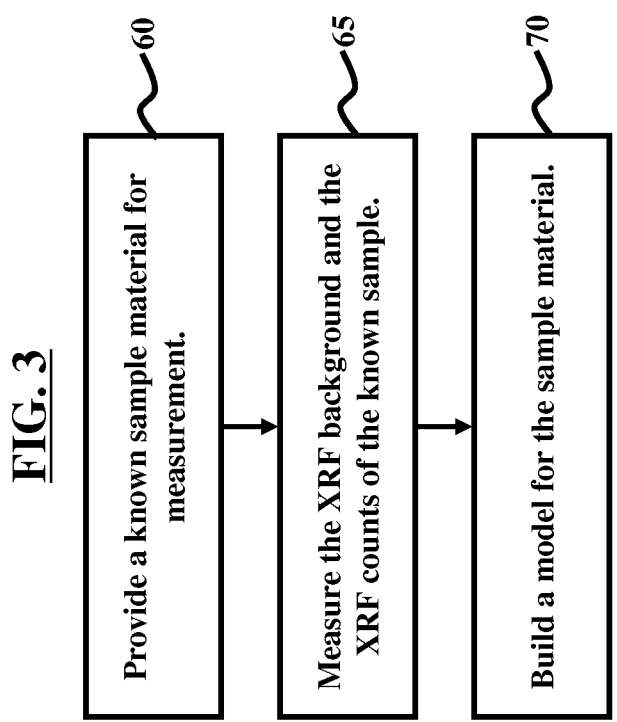
FIG. 3 illustrates flow diagram of a step coverage measurement method according to an embodiment herein.

FIG. 3, with reference to FIGS. 1A through 2, illustrates a flow diagram of a step coverage measurement method according to an embodiment herein. In step (60), the method of FIG. 3 includes providing a known sample (e.g., sample 40) for measurement (e.g., using step coverage measurement tool 30). Step (65) measures the XRF background and the XRF counts of the known sample 40. Next, in step (70), the method shown in FIG. 3 builds a model of the known sample material 40 based on the results of step (65). For example, according to one embodiment herein, an XRF model includes a thickness=$A^* \times (XRF_{raw\ count} - B)$, where $A^*$ is a constant related to the known sample material and B is the background noise of the substrate 5 and material composition 10 without a film deposition (e.g., high plateau thin film 15, low plateau thin film 20, and sidewall thin film 25 shown in FIG. 1C). For example, a thin layer of $ZrO_2$ deposited on TiN has the model: thickness=$26.12^*[XRF_{raw\ counts} - 13.9]$ for one embodiment of step coverage measurement tool 30.

Figure 4:
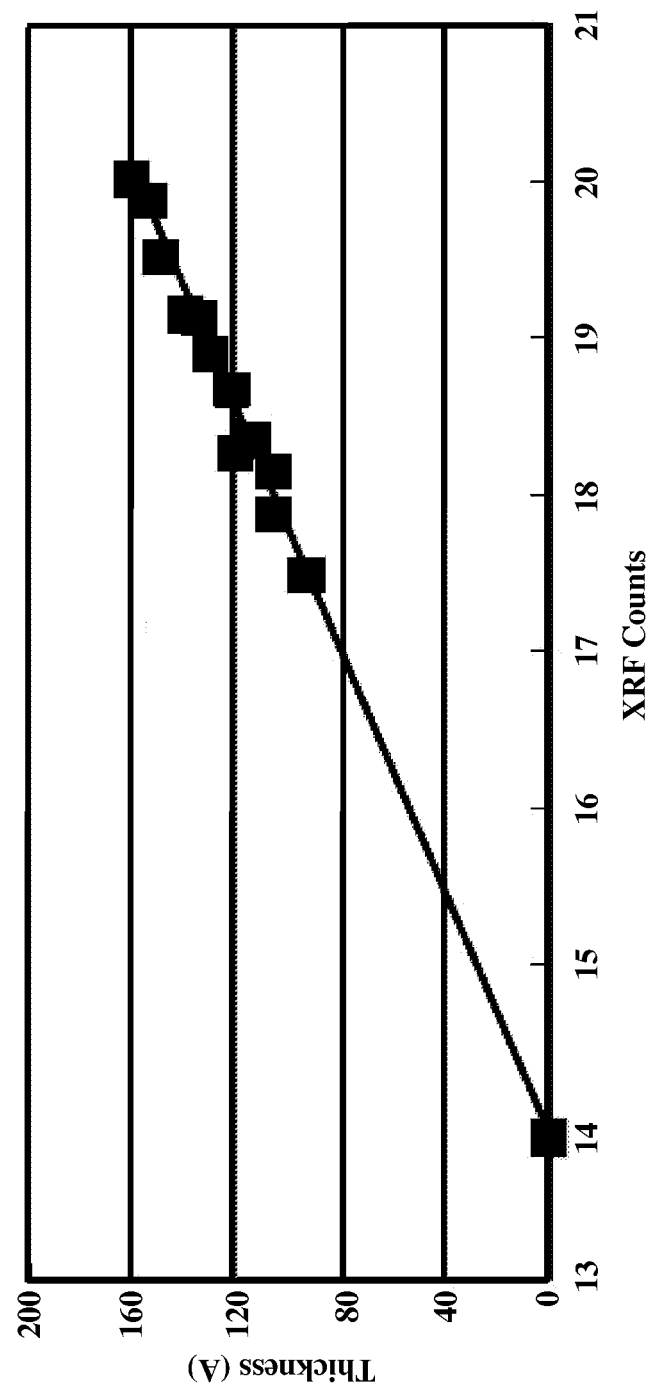
FIG. 4 illustrates sample data of the method shown in FIG. 3 according to an embodiment herein.

FIG. 4, with reference to FIGS. 1A through 3, illustrates sample data generated using the method of FIG. 3. In FIG. 4, the method shown in FIG. 3 is used to determine the thickness of $ZrO_2$ over a substrate (e.g., over substrate 5). FIG. 4 illustrates the thickness plot as a function of XRF raw counts intensity. As shown in FIG. 4, one embodiment of the model derived in step (70) of the method illustrated in FIG. 3 is a linear equation, which can be used as a model to calculate the film thickness. In particular, the x-intercept shown in FIG. 4 illustrates the background noise and the remaining measurements are near linear approximations from that x-intercept.

Figure 5:
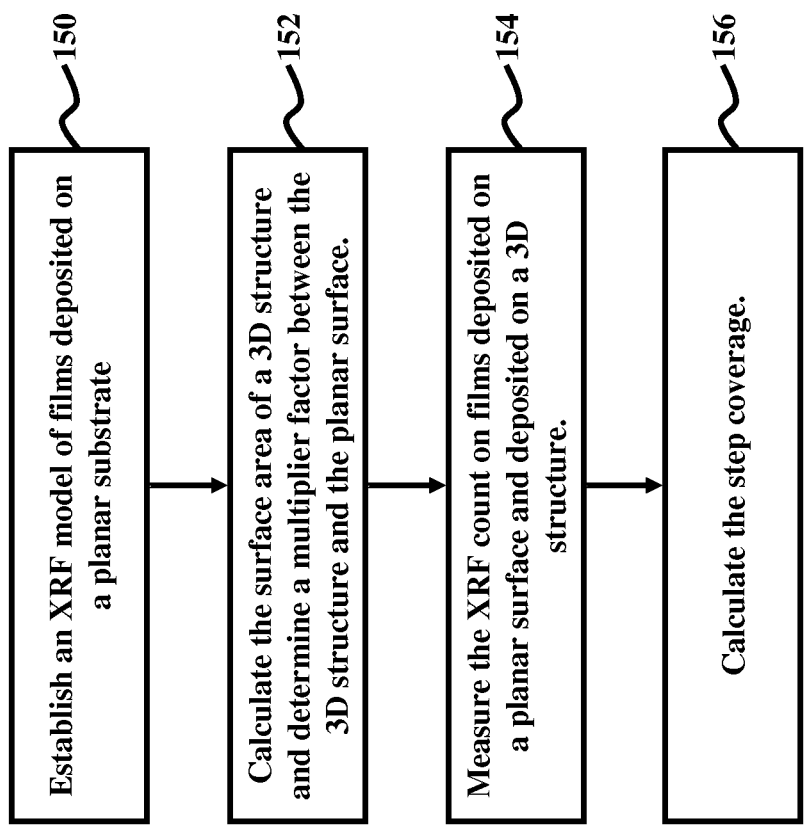
FIG. 5 illustrates a flow diagram of a 3D structure step coverage measurement method according to an embodiment herein.

FIG. 5, with reference to FIGS. 1A through 4, illustrates a flow diagram of a 3D structure step coverage measurement method according to an embodiment herein. In step (150), the method of FIG. 5 establishes an XRF model (e.g., step (70) of the method shown in FIG. 3) for films (e.g., thin film 4 shown in FIG. 1B) deposited on a planar substrate (e.g., substrate 3 shown in FIG. 1B). In addition, the planar substrate 3 has the same process conditions as an unknown 3D structure (e.g., device 2 of FIG. 1C). Step (152) calculates the surface area of the 3D structure (e.g., device 2) and determines a multiplier factor (N) between the 3D structure (e.g., device 2, with high plateau thin film 15 and low plateau thin film 20) and the planar substrate (e.g., thin film 4 on substrate 3). The multiplier factor N is defined as the ratio of XRF counts (i.e., $Count_1$) from a thin film (high plateau thin film 15, low plateau thin film 20, and sidewall thin film 25) deposited on a 3D structure (e.g., device 2) with step coverage (SC) of 100% to the XRF counts (i.e., $Count_0$) from the thin film 4 deposited on a planar wafer (i.e., substrate 3) with the same film thickness. Therefore, the multiplier factor N is proportional to the actual surface area ratio of a 3D structure (e.g., device 2) to a planar wafer (e.g., device 1). For example, assuming the 3D structure (e.g., device 2) contains n holes with a depth of A and a diameter of B (Aspect ratio of A/B) in the unit planar surface area, the multiplier factor N is equal to $(1+\pi*A*B*n)$ and indicates that the surface area is increased by a factor of $(1+\pi*A*B*n)$ due to the existence of deep holes on the 3D wafer 112. Moreover, if the step coverage is less than 100% (i.e., the film thickness of high plateau film 15, sidewall film 25, and low plateau film 20 are not the same), the ratio of XRF counts of a 3D wafer ($Count_1$) to the XRF counts of a planar film ($Count_0$) is less than $(1+\pi*A*B*n)$. Furthermore, in one embodiment herein, the thickness of the sidewall film 25 is assumed to be linearly distributed from high plateau thin film 15 (shown in FIG. 1C) at the top to the bottom of low plateau thin film 20 (shown in FIG. 1C). Therefore, the ratio of XRF counts from a 3D wafer ($Count_1$) to the XRF counts of a planar film ($Count_0$) has the relation: $Count_1/Count_0 = (1-n\pi B^2/4)*SC + n\pi AB(1+SC)/2 + \pi B^2/4*SC$. If the density of holes on the 3D wafer (N) is high and the multiplier factor N is much larger than 1, the count ratio is approximately equal to: $Count_1/Count_0 = n\pi AB(1+SC)/2$, which has a linear relation with the step coverage.

Next, in step (154), the method shown in FIG. 5 measures the XRF count on films (e.g., thin film 4 shown in FIG. 1B, using step coverage measurement tool 30 shown in FIG. 2) deposited on a planar substrate 3 and on a 3D structure (e.g., device 2 including high plateau thin film 15, low plateau thin film 20, and sidewall thin film 25 shown in FIG. 1C). Additionally, one embodiment of the method shown in FIG. 5 uses existing XRF measurement equipment (not shown) to perform the XRF measurement in step (154). In step (156), the method of FIG. 5 calculates the step coverage of the 3D structure (e.g., device 2, with high plateau thin film 15 and low plateau thin film 20) measured in step (154). For example, according to one embodiment herein, $$\text{step coverage} = \frac{count_1/count_0}{N} \times 100,$$

where $count_0$ is the XRF count on a planar surface (e.g., as measured in step (150)), $count_1$ is the XRF count on a 3D surface (e.g., as measured in step (154)), and N is a multiplier factor (e.g., as determined in step (152)).

Figure 6:
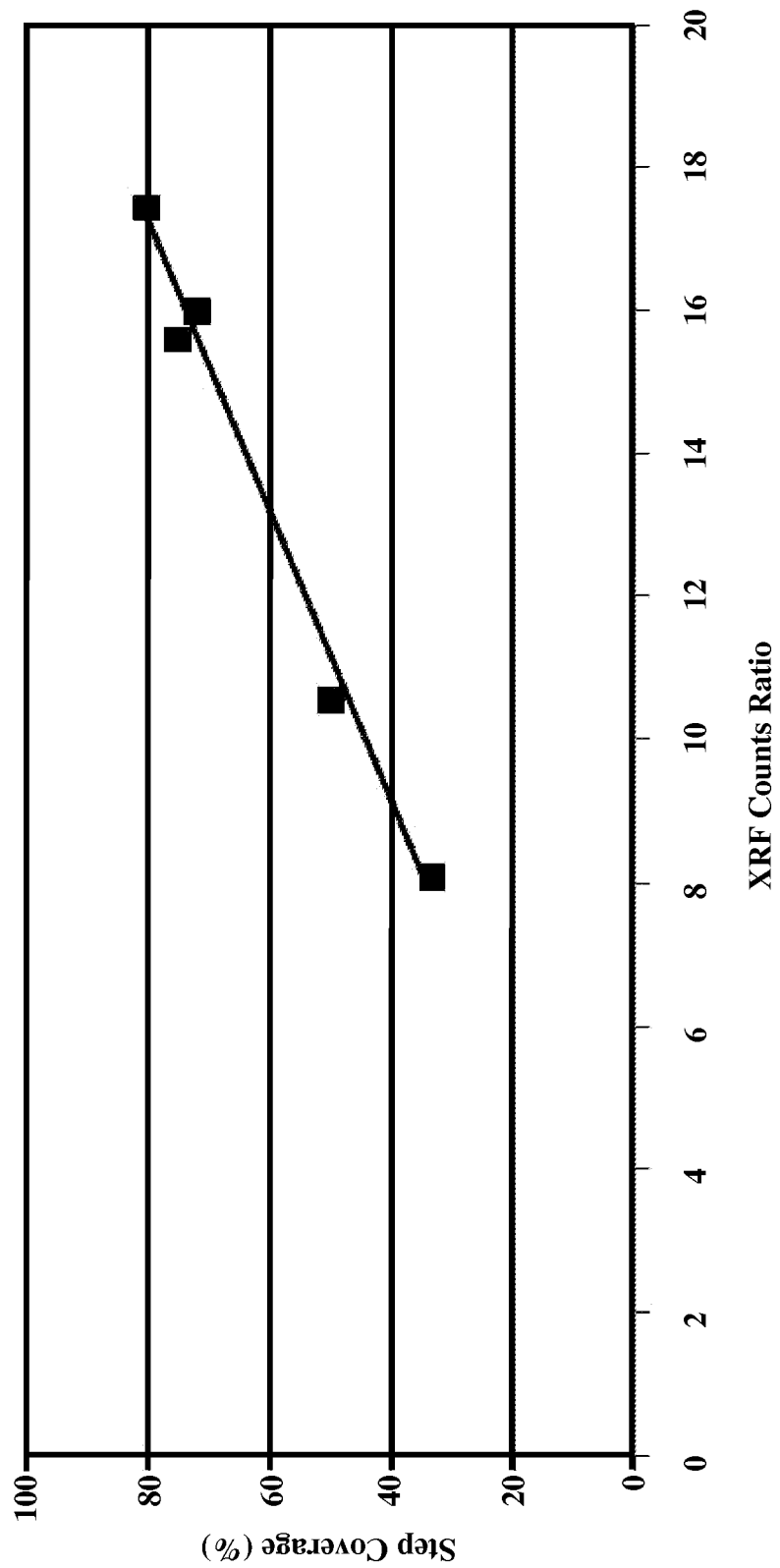
FIG. 6 illustrates sample data of the method shown in FIG. 5 according to an embodiment herein.

FIG. 6, with reference to FIGS. 1A through 5, illustrates sample data using the method of FIG. 5. In FIG. 6, the sample includes a thin film of $ZrO_2$ (e.g., using ALD) deposited on a 3D DRAM structure as a function of the XRF ratio (i.e., the XRF counts of films on a 3D structure/XRF counts on a planar surface). As shown in FIG. 6, one embodiment of the equation derived in step (156) of the method illustrated in FIG. 5 is a linear equation.

Figure 7:
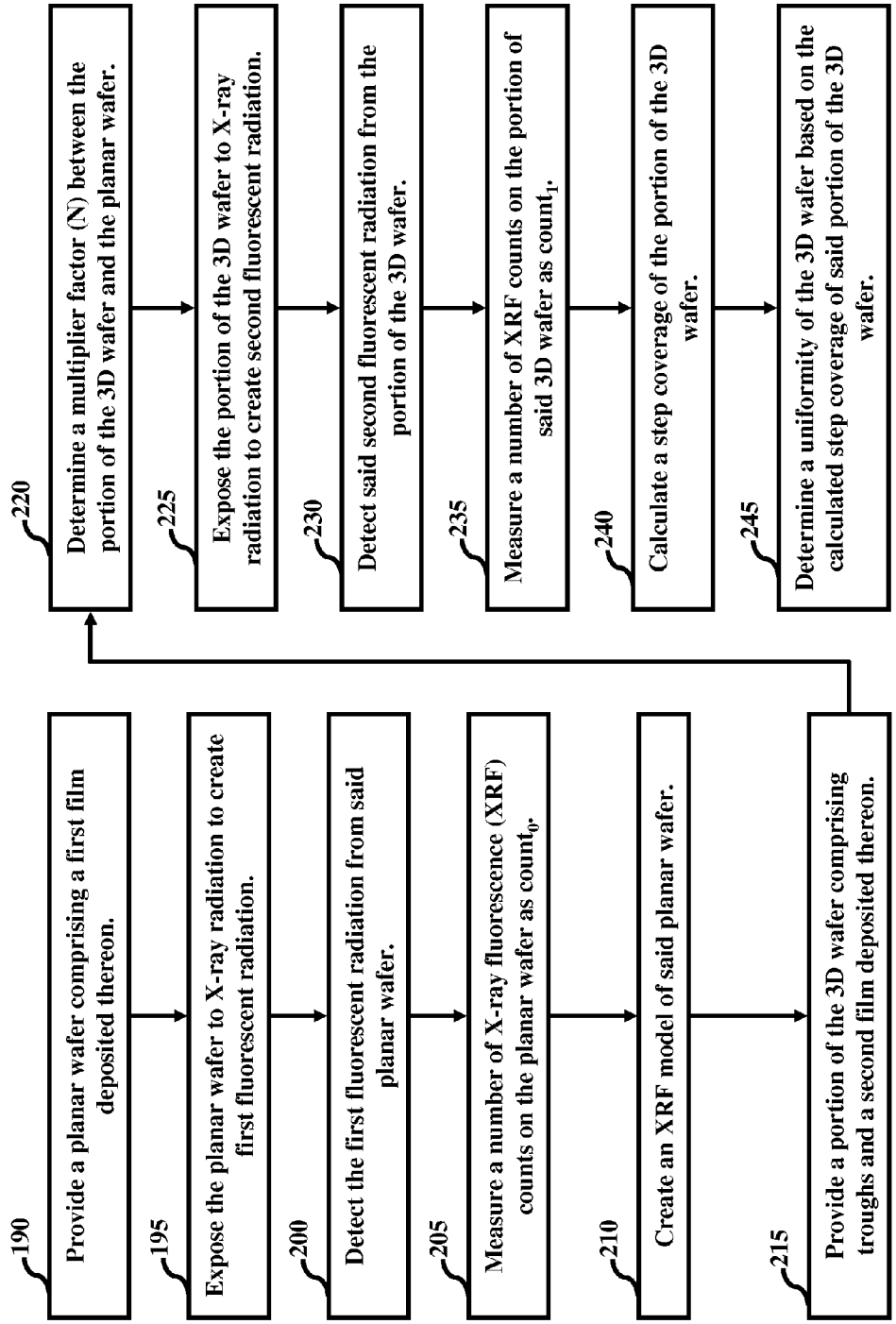
FIG. 7 illustrates a flow diagram of another testing method according to an embodiment herein.

FIG. 7, with reference to FIGS. 1A through 6, illustrates a flow diagram of another testing method according to the embodiments herein. The method includes determining (190) an unknown step coverage of a thin film (e.g., high plateau thin film 15 or low plateau thin film 20) deposited on a 3D wafer (e.g., device 2) that includes providing a planar wafer (e.g., device 1) comprising a first film (e.g., planar thin film 4) deposited thereon. Next, the method includes exposing (195) the planar wafer (e.g., device 1) to X-ray radiation to create first fluorescent radiation (e.g., step 195); detecting (200) the first fluorescent radiation from the planar wafer (e.g., device 1); measuring (205) a number of X-ray fluorescence (XRF) counts on the planar wafer (e.g., device 1) as $count_0$; creating (210) an XRF model of the planar wafer (e.g., device 1); providing (215) a portion of the 3D wafer (e.g., device 2) comprising troughs (e.g., troughs 12) and a second film (e.g., high plateau thin film 15 or low plateau thin film 20) deposited thereon; and determining (220) a multiplier factor (N) between the portion of the 3D wafer (e.g., device 2) and the planar wafer (e.g., device 1).

Thereafter, the method involves exposing (225) the portion of the 3D wafer (e.g., device 2) to X-ray radiation to create second fluorescent radiation; detecting (230) the second fluorescent radiation from the portion of the 3D wafer (e.g., device 2); measuring (235) a number of XRF counts on the portion of the 3D wafer (e.g., device 2) as $count_1$; calculating (240) a step coverage of the portion of the 3D wafer (e.g., device 2, where the calculation may use $$\frac{count_1/count_0}{N} \times 100;$$

and determining (245) a uniformity of the 3D wafer (e.g., device 2) based on the calculated step coverage of the portion of the 3D wafer (e.g., device 2).

Figure 8:
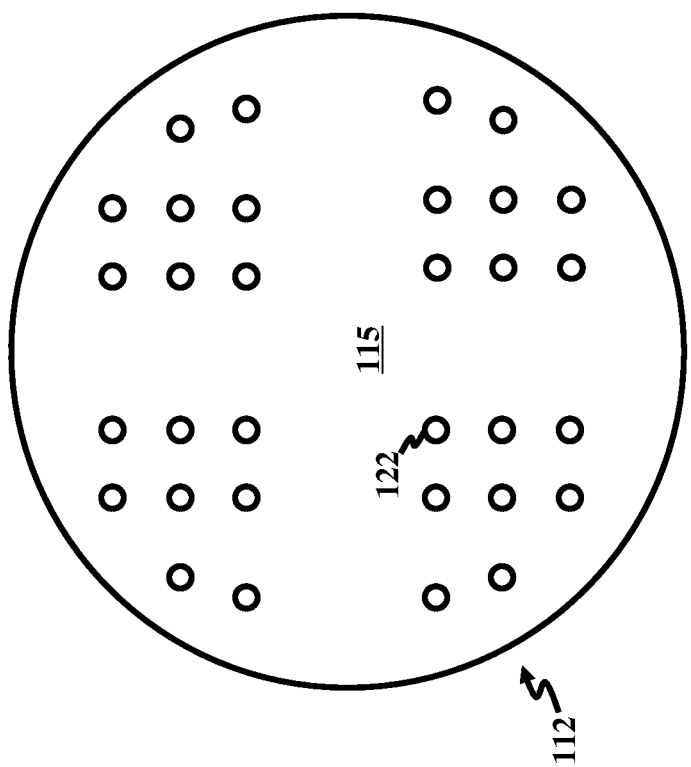
FIG. 8 illustrates a schematic diagram of a wafer step coverage measurement map according to an embodiment herein.

FIG. 8, with reference to FIGS. 1A through 7, illustrates a schematic diagram of a wafer step coverage measurement map according to an embodiment herein. As shown in FIG. 7, wafer 112 includes thin film surface 115, which includes 3D structures (e.g., device 2 shown in FIG. 1C or sample 40 shown in FIG. 2) and a plurality of spot check locations 122. Each spot check location 122, according to one embodiment herein, represents an area where an XRF step coverage measurement is taken (e.g., using the method illustrated in FIG. 5). Consequently, the step coverage for the entire surface of wafer 112 can be calculated using the step coverage of 3D structures (e.g., device 2 shown in FIG. 1C or sample 40 shown in FIG. 2) of each spot check location 122 and the average step coverage over all spot check locations 122 can also be similarly calculated.

Figure 9:
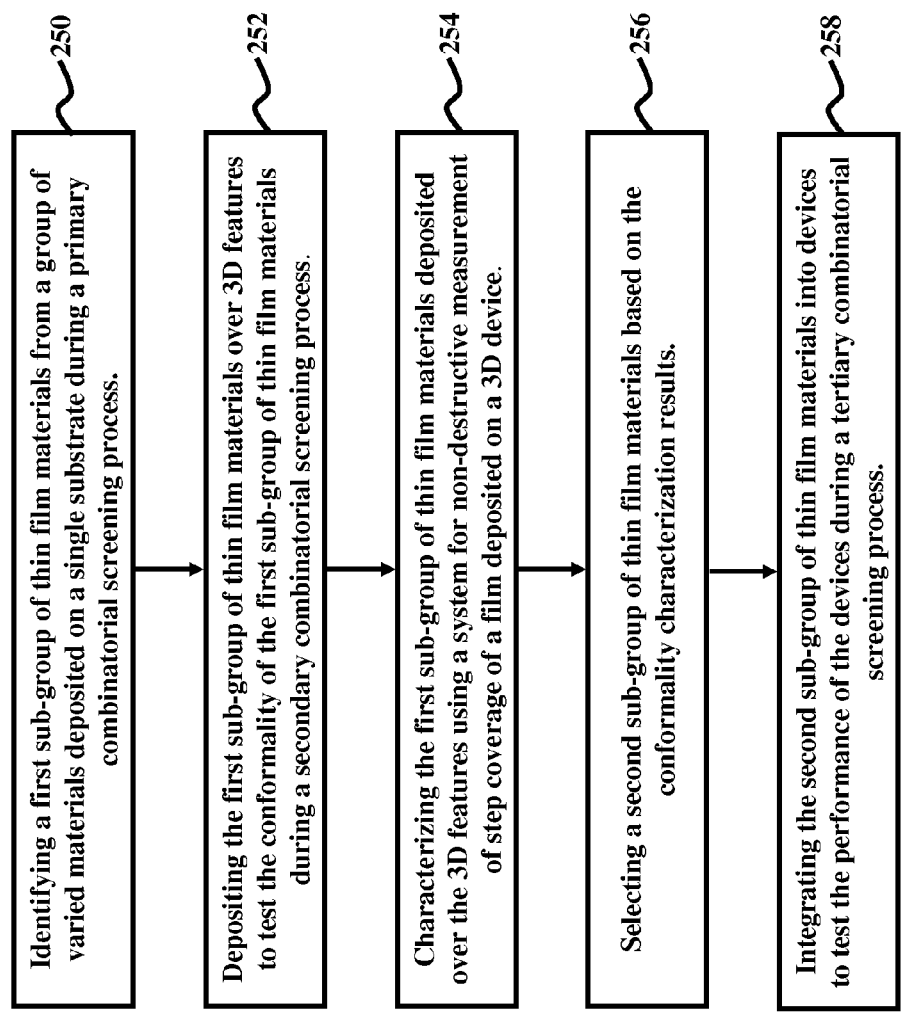
FIG. 9 illustrates a flow diagram of a method of processing according to an embodiment herein.

FIG. 9, with respect to FIGS. 1A through 8, illustrates a flowchart of a method of processing comprising identifying (250) a first sub-group of thin film materials (i.e., thin films deposited on devices 2a) from a group of varied materials deposited on a single substrate 5 during a primary combinatorial screening process (110), the thin film materials (i.e., thin films deposited on devices 2a) having a first set of characteristics. The method further includes depositing (252) the first sub-group of thin film materials (i.e., thin films deposited on devices 2a) over 3D features (i.e., device 2 including the series of troughs 12 or sample 40) to test the conformality of the first sub-group of thin film materials (i.e., thin films deposited on devices 2a) during a secondary combinatorial screening process ((120)).

Next, the method includes characterizing (254) the first sub-group of thin film materials (i.e., material composition 10) deposited over the 3D features (i.e., device 2 including the series of troughs 12 or sample 40) using a system (i.e., tool 30) for non-destructive measurement of step coverage of a film (e.g., films 15, 20, 25 of FIG. 1C) deposited on a 3D device (e.g., device 2 or sample 40). The system (i.e., tool 30) comprises an emitter 35 that emits radiation comprising sufficient energy necessary to excite the 3D device (e.g., device 2 or sample 40) to fluorescence; a detector 45 that detects the fluorescence from the 3D device (e.g., device 2 or sample 40); and a quantifier 50 that quantifies the fluorescence from the 3D device (e.g., device 2 or sample 40) and applies a step coverage model to determine the step coverage of the film (e.g., films 15, 20, 25 or 115). Thereafter, the method includes selecting (256) a second sub-group of thin film materials (i.e., thin films deposited on devices 2b) based on the conformality characterization results; and integrating (258) the second sub-group of thin film materials (i.e., thin films on devices 2b) into wafer 112 to test the performance of the wafer 112 during a tertiary combinatorial screening process (130).

The embodiments herein provide a step coverage measurement tool 30 and method (e.g., the methods of FIGS. 1E, 3, 5, 7, and 9) that permit a non-destructive measurement of a sample's (e.g., sample 40, shown in FIG. 2, as prepared using combinatorial processes) step coverage (e.g., as shown in FIG. 1C). In addition, the tool 30 and methods provide greater efficiency (e.g., less time to conduct the measurements because the measurements are non-destructive) and speed (e.g., due to the speed at which XRF measurements are conducted) over conventional systems. In addition, combinatorial processes and material discovery processes are improved because a sample material (e.g., sample 40) may undergo multiple non-destructive tests (e.g., using step coverage measurement tool 30). The embodiments herein provide this measurement at a lower cost (e.g., reuse of device 2 after step coverage measurement has been taken and the proliferation of existing XRF equipment) when compared to conventional systems.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of several embodiments, those skilled in the art will recognize that the embodiments herein can be practiced with modification within the spirit and scope of the appended claims.

What is claimed is:

1. A method of characterizing a film on a 3D device, comprising:
    exposing the film to radiation of sufficient energy to excite secondary X-ray emission from the film;
    detecting the emission from the film;
    quantifying the emission as a $count_1$;
    retrieving a $count_0$;
    determining a multiplier factor N; and
    calculating a step coverage;
    wherein the $count_0$ is derived from a measurement of secondary X-ray emission from a planar device;
    wherein the multiplier factor N is derived from an actual surface area of the film on the 3D device;
    wherein the step coverage comprises a ratio resulting from the division of the count1 by the count0;
    and wherein the calculating of the step coverage further comprises multiplying the ratio by the multiplier factor N.

2. The method of claim 1, wherein the radiation comprises high-energy X-rays, gamma rays, or short-wavelength X-rays.

3. The method of claim 1, wherein the emission is detected by a photomultiplier.

4. The method of claim 1, wherein the multiplier factor N is proportional to the actual surface area ratio of the 3D device and the planar device.

5. The method of claim 1, wherein the multiplier factor N is equal to $(1+\pi ABn)$
    wherein A is a depth of a hole in the 3D device;
    wherein B is a diameter of the hole in the 3D device; and
    wherein n is a quantity of holes within the 3D device.

6. The method of claim 5, further comprising:
    assuming a thickness of a sidewall portion of the film is linearly distributed from a high plateau value to a low plateau value; and
    calculating the step coverage SC by $count_1/count_0 = (1-n\pi B^2/4)SC + n\pi AB(1+SC)/2 + n\pi B^2 SC/4$.

7. The method of claim 5, wherein the multiplier factor N is much greater than 1; and wherein the step coverage SC is calculated by $count_1/count_0 = n\pi AB(1+SC)/2$.

8. The method of claim 1, wherein the step coverage linearly increases with a ratio of the $count_1$ to the $count_0$.

* * * * *